(12) United States Patent
Doan et al.

(10) Patent No.: US 6,183,305 B1
(45) Date of Patent: Feb. 6, 2001

(54) HIGH STRENGTH CONNECTOR DESIGN FOR PASSIVE FIXATION PACING LEAD

(75) Inventors: Phong D. Doan, Stevenson Ranch; Eric M. Lorenzen, Granada Hills, both of CA (US)

(73) Assignee: Pacesetter, Inc., Sylmar, CA (US)

( * ) Notice: Under 35 U.S.C. 154(b), the term of this patent shall be extended for 0 days.

(21) Appl. No.: 09/205,966

(22) Filed: Dec. 4, 1998

(51) Int. Cl.$^7$ ............................. H01R 24/04; H01R 13/73
(52) U.S. Cl. ............................................. 439/668; 439/909
(58) Field of Search ................................. 439/335, 891, 439/909, 668, 669; 607/116, 119, 122, 37; 200/51.02

(56) References Cited

U.S. PATENT DOCUMENTS

| | | | |
|---|---|---|---|
| 1,021,195 | 3/1912 | Knauff | 200/51.02 |
| 1,753,179 | 4/1930 | Wertz | 439/335 |
| 2,947,966 | 8/1960 | Francis et al. | 439/335 |
| 3,397,377 | 8/1968 | Potter | 439/279 |
| 3,757,789 | 9/1973 | Shanker | 607/37 |
| 4,381,014 | 4/1983 | Sandstrom et al. | 607/119 |
| 4,886,074 | 12/1989 | Bisping | 607/116 |
| 5,230,634 | 7/1993 | Yamaguchi et al. | 439/149 |
| 5,304,219 | * 4/1994 | Chernoff et al. | 307/122 |
| 5,383,922 | 1/1995 | Zipes et al. | 607/122 |
| 5,514,172 | 5/1996 | Mueller | 607/122 |
| 5,531,781 | 7/1996 | Alferness et al. | 607/122 |
| 5,782,900 | 7/1998 | de la Rama et al. | 607/122 |
| 5,807,144 | 9/1998 | Sivard | 439/816 |
| 5,968,082 | * 10/1999 | Heil | 607/37 |
| 6,006,137 | * 12/1999 | Williams | 607/119 |

* cited by examiner

*Primary Examiner*—Brian Sircus
*Assistant Examiner*—Chandrika Prasad

(57) ABSTRACT

A connector assembly located at the proximal end of an elongated lead body includes first and second electrical contacts, each attached to a respective one of at least two conductors. An interlocking construction positively joins the first and second electrical contacts and maintains a fixed axial spacing therebetween. The first connector includes a connector pin having a head portion at an extremity thereof and an integral and coaxial tail portion and the second connector includes a connector ring coaxial with and telescopingly received on the tail portion. An electrically insulative male joint member integral with the tail portion is selectively lockingly engageable with a female joint member integral with the connector ring. Diametrically opposed knob members project radially from an outer peripheral surface of the male joint member and slidably engage a pair of diametrically opposed longitudinal slots in an integral axial sleeve extending proximally from the second electrical contact, the longitudinal slots terminating at a pair of oppositely extending circumferential slots. The electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob members are slidably engaged with the longitudinal slots, then rotating the tail portion so that the knob members are slidably engaged with the circumferential slots.

13 Claims, 5 Drawing Sheets

HIGH STRENGTH CONNECTOR DESIGN FOR PASSIVE FIXATION PACING LEAD

FIELD OF THE INVENTION

The present invention relates generally to electrical leads for connecting implantable medical devices with selected body tissue to be stimulated by such devices, and more particularly to a strengthened connector assembly located at the proximal end of a lead body which positively joins first and second electrical contacts, each attached to a respective one of a pair of conductors of the lead body and maintains a fixed axial spacing between the contacts.

BACKGROUND OF THE INVENTION

Implantable electronic devices are in use providing electronic pulses to stimulate tissue via a lead extending from an implanted pulse generator to a desired internal location. An example of this type of technology is a pacemaker and a pacing lead which provides electrical stimulation to the heart. The pacemaker is usually implanted in a subcutaneous cavity, and the leads extend either transvenously to the internal cavities of the heart, or to patch electrodes located on external surface of the heart.

The leads generally include at least one, and often two or more, electrodes located at a distal end, and a connector having a similar number of electrical connector elements for interconnection to the pulse generator at the proximal end. The electrical connector elements, or contacts, at the proximal end and the distal electrodes are interconnected by conductors extending through an insulated lead body. It is common for the leads to include helically wound conductors which are either coaxially mounted or side-by-side wound within the lead body, separated by insulation.

The connector is inserted into a receiving orifice in a header portion of the pulse generator. The header portion of the pulse generator may be formed from an epoxy material which is assembled and bonded to the main body of the pulse generator. The main body of the pulse generator is generally a metallic self-contained housing or can, which encloses the source of electrical energy and electrical circuitry for controlling the electrical stimulus delivered by the lead.

In the design of the lead connector and the pulse generator, it is important for the lead to be safely secured to the pulse generator to prevent inadvertent decoupling. Generally, connectors have been assembled using flexible insulation materials to separate the respective electrical components. Problems which arise in the construction and use of multiple conductor lead connectors are primarily related to the design of the electrical interconnection between the conductors and the contacts. The connector must be constructed in a manner which prevents fluids from invading the connector and shorting the electrical conductors therein.

The strength of the existing IS-1 connector widely used in the current generation of passive fixation pacing leads is adequate for a normal usage condition. However, when the connector is adversely misused, the connector pin may be separated away from the connector. For example, an attempt to withdraw the connector pin from the pacer header while a setscrew commonly used to firmly affix it to the header is inadvertently forgotten to be unfastened, may result in a connector pin to connector separation. The connector design of the invention serves to strengthen this potentially weak region, thereby minimizing the problem. Also, the locking mechanism simplifies the assembly process as well as making it more repeatable. Currently, the parts have freedom to move during and after the bonding process. With the design of the invention, however, the parts are locked in place and are unable to move relative to each other during subsequent bonding operations.

A number of patents are representative of the prior art in this regard.

U.S. Pat. No. 5,807,144 to Sivard discloses a device for affixing an elongate contact pin on an electrode lead for connection to a medical implant containing an elongate connector part with an opening at one end into which the contact pin can be inserted. The connector part has an affixing part which, when acted on by the contact pin, can move in the connector part's longitudinal direction between a contact pin-affixing position and a contact pin-release position.

U.S. Pat. No. 5,782,900 to de la Rama et al. discloses safety anchoring pins on a tip electrode to match receptacle holes on a catheter shaft and/or the extended flexible stem on the tip electrode maintains the integrity of the catheter system from potential complications of undesired components disengagement.

U.S. Pat. Nos. 5,531,781 to Alferness et al. and 5,383,922 to Zipes et al., disclose a connection means of the pin and groove type but do not specifically spell out the connection.

U.S. Pat. No. 5,514,172 to Mueller discloses a ring connector with deflectable circular elements which engage with holes in a rigid insulator to produce a connection for a multi-conductor lead device.

U.S. Pat. Nos. 3,397,377 to Potter; 2,947,966 to Francis et al.; and 1,021,195 to Knauff all disclose circular connector bodies outside of the field of the invention and having bayonet type slots for engagement by pins or the like.

It was with knowledge of the foregoing state of the technology that the present invention has been conceived and is now reduced to practice.

SUMMARY OF THE INVENTION

The present invention, as disclosed and claimed, relates to a connector assembly located at the proximal end of an elongated lead body which includes first and second electrical contacts. Each electrical contact is attached to a respective one of at least two conductors. An interlocking construction positively joins the first and second electrical contacts and maintains a fixed axial spacing between the contacts. The first contact includes a connector pin having a head portion at an extremity thereof and an integral and coaxial tail portion and the second contact includes a connector ring coaxial with and telescopingly received on the tail portion. An electrically insulative male joint member integral with the tail portion is selectively lockingly engageable with a female joint member integral with the connector ring. Diametrically opposed knob members project radially from an outer peripheral surface of the male joint member and slidably engage a pair of diametrically opposed longitudinal slots in an integral axial sleeve extending proximally from the second electrical contact, the longitudinal slots terminating at a pair of oppositely extending circumferential slots. The electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob members are slidably engaged with the longitudinal slots, then rotating the tail portion so that the knob members are slidably engaged with the circumferential slots.

The new connector meets all exterior dimensional and functional requirements of the IS-1 standard, a connector configuration which is established and controlled by the International Standards Organization. The connector of the invention features a mechanical locking mechanism between the connector ring and connector pin which substantially improves the composite pull strength between these components.

A primary feature, then, of the present invention is the provision of an improved electrical lead for connecting implantable medical devices with selected body tissue to be stimulated by such devices.

Another feature of the present invention is the provision of such an electrical lead with a strengthened connector assembly located at the proximal end of the lead body.

Still another feature of the present invention is the provision of such an electrical lead which positively joins first and second electrical contacts, each contact being attached to a respective one of a pair of conductors of the lead body and maintaining a fixed axial spacing between the contacts.

Yet another feature of the present invention is the provision of such an electrical lead providing a more robust connector design resulting in less of a problem of separation between connector pin and ring in the operation room.

Still a further feature of the present invention is the provision of such an electrical lead possessing a less expensive design than the existing IS-1 connectors.

Yet a further feature of the present invention is the provision of such an electrical lead having a construction which simplifies the assembly process and, indeed, makes the assembly process more repeatable. Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
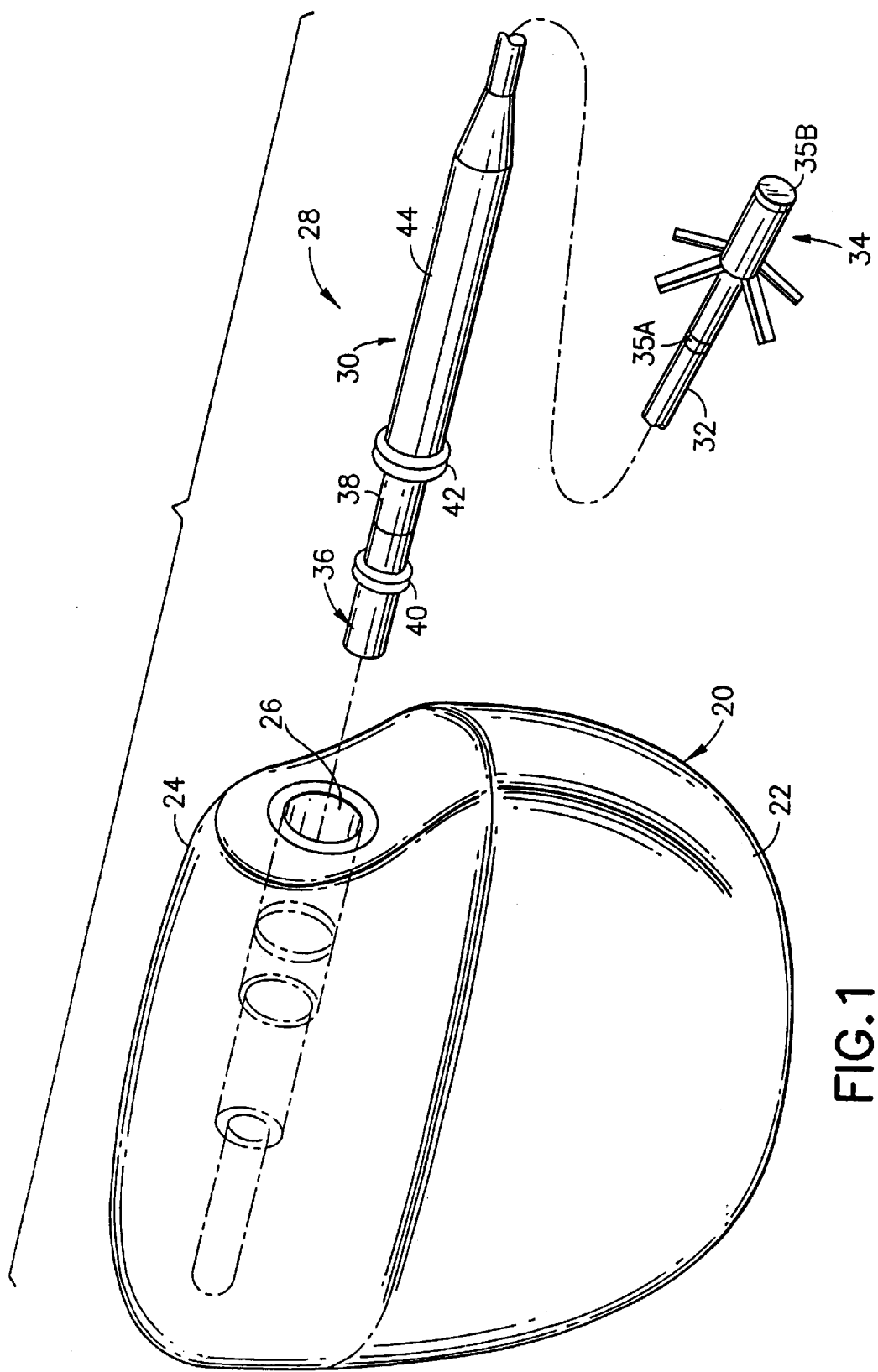
FIG. 1 is a perspective view of the components of a pacing system embodying the invention.

Turn now to the drawings and, initially, to FIG. 1 which generally illustrates an electrical stimulus generating system embodying the present invention. More specifically, FIG. 1 depicts an implantable medical device including a pulse generator 20 such as a pacemaker, which includes a hermetically sealed housing 22 containing the power supply and electronic circuitry (not shown) of the pulse generator, and an attached header 24 including at least one connector receiving orifice 26. The header 24 may be either integral with the housing 22, or formed as a separate element and suitably attached to the housing. It should be noted that the pulse generator 20 may have two or more orifices for receiving the connectors of two or more leads, if required.

Also depicted in FIG. 1 is a pacing lead 28 including a connector assembly 30 at a proximal end designed to be inserted into the receiving orifice 26 of the pulse generator 20. The pacing lead 28 further includes a lead body 32 with at least two conductors 33A, 33B (see FIG. 2) extending from its proximal end connection to the connector assembly 30 to an electrode assembly 34 at the distal end of the lead body 32. The electrode assembly 34, which includes a pair of spaced, electrically isolated, electrodes, namely, a ring electrode 35A and a tip electrode 35B, is designed to deliver electrical stimuli to the implant situs. While the design of the connector assembly 30 detailed herein is described in connection with a pacing lead, it should be understood that the connector assembly 30 may be incorporated into other types of leads, such as sensor leads and defibrillation leads having differing electrode assemblies.

Figure 2:
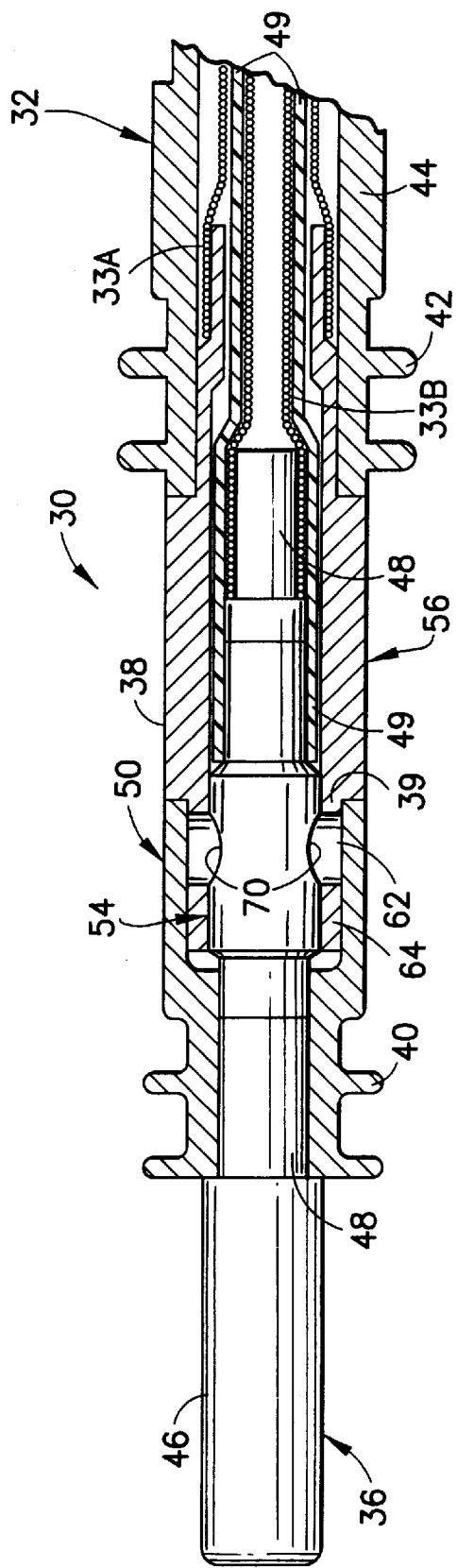
FIG. 2 is a detail elevation view, partially in section, of a connector assembly, one of the components illustrated in FIG. 1.

As illustrated in FIGS. 1 and 2, the connector assembly 30 includes a pair of electrical contacts 36, 38, each attached to a respective one of the two conductors 33A, 33B of the lead body 32, as well as seal members 40 and 42, and a lead boot 44, integral with and extending from, the seal member 42. FIG. 2 depicts a cross sectional view of the connector assembly 30 detailing the design of the sub-components which comprise the proximal portion of the connector assembly 30.

Proceeding distally (to the right, viewing FIGS. 2, 3 and 4) from the electrical contact 36, or connector pin, the connector pin is seen to include a generally cylindrical head portion 46 at an extremity thereof and a tail portion 48 integral and coaxial with the head portion. Continuing rightwardly, the electrical contact 38 includes a connector ring 39 coaxial with and telescopingly received on the tail portion 48 of the connector pin 36.

The seal member 40 is intermediate the electrical contacts 36, 38 and overlies the tail portion 48 of the connector pin 36 and serves to engage the receiving orifice 26 of the pulse generator 20. The seal member 42, coaxial with the seal member 40, is positioned adjacent the electrical contact 38 and distant from the seal member 40 and also serves to engage the receiving orifice of the pulse generator 20. Additionally, an insulating sleeve 49 surrounds the conductor 33B and electrically isolates it from the conductor 33A.

As a primary feature of the invention, the pacing lead 28 includes an interlocking mechanism 50 (FIG. 2) for positively joining the electrical contacts 36, 38 while keeping them electrically isolated and maintaining a fixed axial spacing between them. Viewing FIG. 3, the tail portion 48 of the connector pin 36 has an elongated annular groove 52 spaced from the head portion 46. The interlocking mechanism 50 includes an electrically insulative male joint member 54 (FIG. 3) integral with the tail portion 48 of the connector pin 36 and a female joint member 56 (FIGS. 5 and 6) integral with the connector ring 39 selectively lockingly engageable with the male joint member.

Figure 3A:
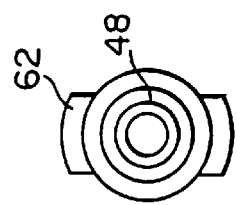
FIG. 3A is an end elevation view of the component illustrated in FIG. 3.
Figure 3:
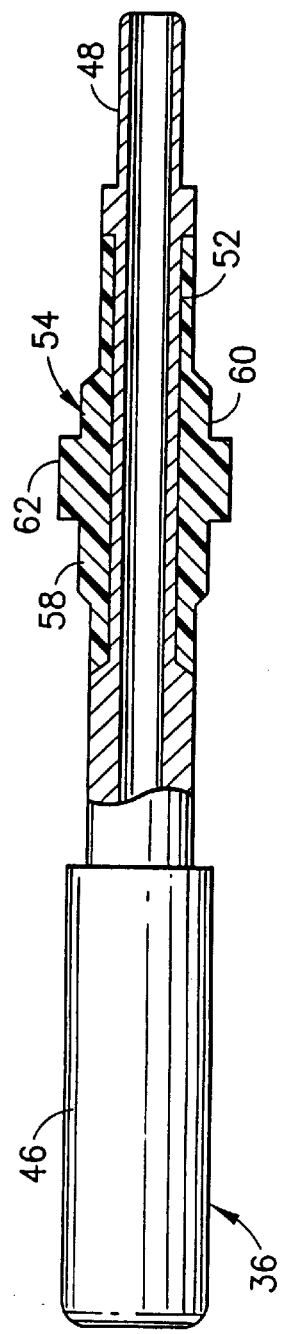
FIG. 3 is a detail elevation view, partially in section, of one of the components of the connector assembly illustrated in FIG. 2.
Figure 4:
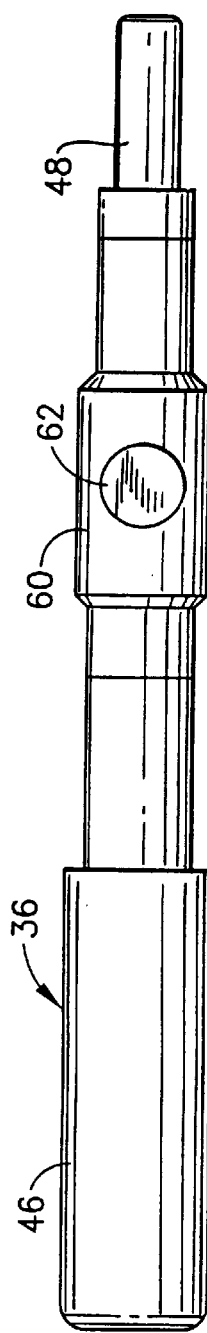
FIG. 4 is a detail top plan view of the component illustrated in FIG. 3.

As most clearly seen in FIG. 3, the male joint member 54 includes an overmolded thermoplastic dielectric element 58 contiguous with the elongated annular groove 52. The dielectric element 58 which may be, for example, of a polysulfone or polyurethane or of some other suitable material, has an outer peripheral surface 60 from which radially project a pair of diametrically opposed knob members 62.

Figure 5B:
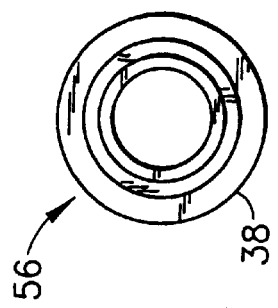
FIGS. 5A and 5B are end elevation views of the component illustrated in FIG. 5, taken, respectively, from opposite ends of the component.
Figure 5:
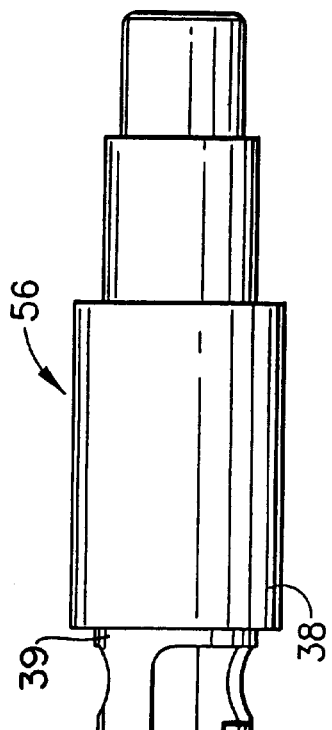
FIG. 5 is a detail elevation view, partially in section, of another of the components of the connector assembly illustrated in FIG. 2.
Figure 5A:
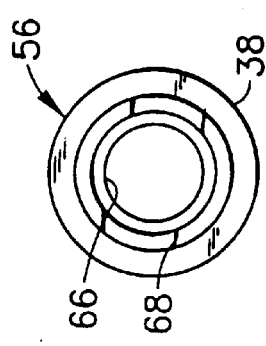
Figure 6:
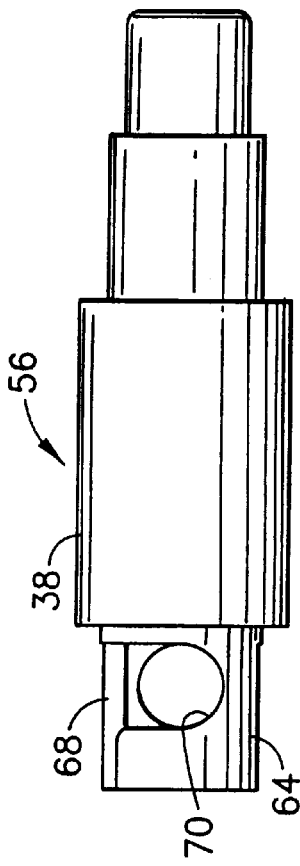
FIG. 6 is a detail top plan view of the component illustrated in FIG. 5.

As most clearly seen in FIGS. 5 and 6, the female joint member 56 includes an axial sleeve 64 integral with and extending proximally (to the left, viewing FIGS. 5 and 6) from the electrical contact 38, the axial sleeve including an inner peripheral surface 66 having a pair of diametrically opposed longitudinal slots 68 (FIGS. 5, 5A, and 6) terminating at a pair of oppositely extending circumferential slots 70 (FIG. 6) sized for engageably but slidably receiving the knob members 62 of the male joint member 54.

With the construction just described, the electrical contacts 36 (connector pin) and 38 (connector ring 39) are positively joined by axially aligning the connector pin and the connector ring while they are initially held spaced apart. Then the tail portion 48 of the connector pin 36 is advanced on axis toward the connector ring 39 so that the outer peripheral surface 60 of the male joint member 54 becomes fittingly engaged with the inner peripheral surface 66 of the axial sleeve 64 and so that the knob members 62 are aligned with and engaged with the longitudinal slots 68. When the knob members 62 reach the ends of the longitudinal slots 68, the tail portion 48 is then rotated so that the knob members become engaged with the circumferential slots 70.

Figure 7:
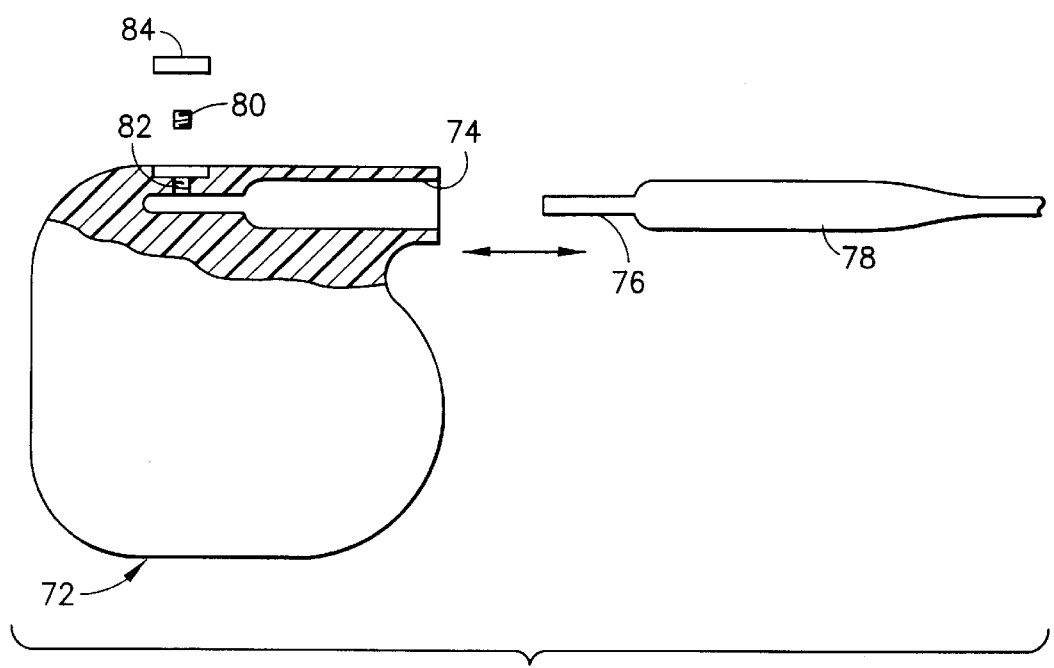
FIG. 7 is a side elevation view of the components of a known pacing system.

With this construction, an electrical lead is provided which positively joins first and second electrical contacts, each contact being attached to a respective one of a pair of conductors of the lead body while maintaining them electrically isolated with a fixed axial spacing between them. The present invention thus contrasts with a typical known construction illustrated in FIG. 7. In this instance, a known pulse generator 72 has a receiving orifice 74 into which is inserted a connector pin 76 of a pacing lead 78. When the connector pin 76 is fully inserted into the receiving orifice 76, it is customary to tighten a set screw 80, which is threadedly engaged with a tapped bore 82, into engagement with the connector pin to hinder its inadvertent removal. In this arrangement, a cap 84 customarily overlies the set screw 80 and tapped bore 82 to assure the sealed integrity of the pulse generator 72. Unfortunately, with this construction, the connector assembly may be adversely misused resulting in the connector pin being separated from the rest of the assembly. For example, an attempt to withdraw the connector pin from the pacer header while the setscrew remains tightened, may result in a connector pin to connector assembly separation. The connector assembly design of the invention strengthens the previously weak region thereby minimizing this problem.

Also, as noted previously, the invention simplifies the assembly process as well as making it more repeatable. Currently, the parts have freedom to move during and after the bonding process. With this new design, the parts will be locked in place and will not move relative to each other during subsequent bonding operations.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable lead extending between proximal and distal ends for delivering an electrical stimulus from a pulse generator to tissue, the implantable lead comprising:

an elongated lead body including at least two conductors extending between the distal end for engagement with the tissue and proximal end for connection to the pulse generator thereof;

at least two axially spaced electrodes adjacent the distal end of the lead body each attached to a respective one of the two conductors of the lead body;

a connector assembly located at the proximal end of the lead body including first and second electrical contacts, each attached to a respective one of the two conductors of the lead body, the first electrical contact including a connector pin having a head portion at an extremity thereof and a tail portion integral and coaxial with the head portion, the second electrical contact including a connector ring coaxial with and telescopingly received on the tail portion of the connector pin; and interlocking means for positively joining the first and second electrical contacts and maintaining a fixed axial spacing therebetween, the interlocking means including an electrically insulative male joint member integral with the tail portion of the connector pin, and a female joint member integral with the connector ring selectively lockingly engageable with the male joint member.

2. An implantable lead, as set forth in claim 1, wherein the male joint member includes an outer peripheral surface having an outer diameter and a pair of diametrically opposed knob members projecting radially from the outer peripheral surface; and wherein the female joint member includes an axial sleeve integral with and extending proximally from the second electrical contact, the axial sleeve including an inner peripheral surface having an inner diameter and a pair of diametrically opposed longitudinal slots terminating at a pair of oppositely extending circumferential slots sized for engageably but slidably receiving the knob members of the male joint member;

whereby the first and second electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob members are slidably engaged with the longitudinal slots, then rotating the tail portion so that the knob members are slidably engaged with the circumferential slots.

3. An implantable lead, as set forth in claim 1, wherein the male joint member includes an outer peripheral surface having an outer diameter and at least one knob member projecting radially from the outer peripheral surface; and wherein the female joint member includes an axial sleeve integral with and extending proximally from the second electrical contact, the axial sleeve including an inner peripheral surface having an inner diameter and at least one longitudinal slot terminating at a circumferential slot sized for engageably but slidably receiving the knob members of the male joint member;

whereby the first and second electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob member is slidably engaged with the longitudinal slot, then rotating the tail portion so that the knob member is slidably engaged with the circumferential slot.

4. An implantable lead, as set forth in claim 1, wherein the tail portion of the connector pin has an elongated annular groove spaced from the head portion thereof; and wherein the male joint member includes an overmolded dielectric element contiguous with the elongated annular groove including an outer peripheral surface having an outer diameter and a pair of diametrically opposed knob members projecting radially from the outer peripheral surface; and wherein the female joint member includes an axial sleeve integral with and extending proximally from the second electrical contact, the axial sleeve including an inner peripheral surface having an inner diameter and a pair of diametrically opposed longitudinal slots terminating at a pair of oppositely extending circumferential slots sized for engageably but slidably receiving the knob members of the male joint member;

whereby the first and second electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob members are engaged with the longitudinal slots, then rotating the tail portion so that the knob members are engaged with the circumferential slots.

5. An implantable lead, as set forth in claim 1, including:

seal means intermediate the first and second electrical contacts for engaging a receiving orifice of the pulse generator.

6. An implantable lead, as set forth in claim 2, including:

first seal means intermediate the first and second electrical contacts and overlying the tail portion of the connector pin for engaging a receiving orifice of the pulse generator; and second seal means adjacent the first electrical contact and distant from the first seal means for engaging a receiving orifice of the pulse generator.

7. A connector assembly located at a proximal end of a lead body, such lead body extending between proximal and distal ends thereof comprising:

first and second electrical contacts, each attached to a respective one of two conductors of an elongated lead body extending between the distal end for engagement with tissue and the proximal end for connection to a pulse generator, the first electrical contact including a connector pin having a head portion at an extremity thereof and a tail portion integral and coaxial with the head portion, the second electrical contact including a connector ring coaxial with and telescopingly received on the tail portion of the connector pin, the second electrical contact including a connector ring coaxial with and telescopingly received on the tail portion of the connector pin; and interlocking means for positively joining the first and second electrical contacts and maintaining a fixed axial spacing therebetween, the interlocking means including an electrically insulative male joint member integral with the tail portion of the connector pin, and a female joint member integral with the connector ring selectively lockingly engageable with the male joint member.

8. A connector assembly, as set forth in claim 7, wherein the first electrical contact includes:

a connector pin having a head portion at an extremity thereof and a tail portion integral and coaxial with the head portion;

wherein the second electrical contact includes:

a connector ring coaxial with and telescopingly received on the tail portion of the connector pin; and wherein the interlocking means includes:

an electrically insulative male joint member integral with the tail portion of the connector pin; and a female joint member integral with the connector ring selectively lockingly engageable with the male joint member.

9. A connector assembly, as set forth in claim 8, wherein the male joint member includes an outer peripheral surface having an outer diameter and a pair of diametrically opposed knob members projecting radially from the outer peripheral surface; and wherein the female joint member includes an axial sleeve integral with and extending proximally from the second electrical contact, the axial sleeve including an inner peripheral surface having an inner diameter and a pair of diametrically opposed longitudinal slots terminating at a pair of oppositely extending circumferential slots sized for engageably but slidably receiving the knob members of the male joint member;

whereby the first and second electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob members are slidably engaged with the longitudinal slots, then rotating the tail portion so that the knob members are slidably engaged with the circumferential slots.

10. A connector assembly, as set forth in claim 8, wherein the male joint member includes an outer peripheral surface having an outer diameter and at least one knob member projecting radially from the outer peripheral surface; and wherein the female joint member includes an axial sleeve integral with and extending proximally from the second electrical contact, the axial sleeve including an inner peripheral surface having an inner diameter and at least one longitudinal slot terminating at a circumferential slot sized for engageably but slidably receiving the knob member of the male joint member;

whereby the first and second electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob member is slidably engaged with the longitudinal slot, then rotating the tail portion so that the knob member is slidably engaged with the circumferential slot.

11. A connector assembly, as set forth in claim 8, wherein the tail portion of the connector pin has an elongated annular groove spaced from the head portion thereof; and wherein the male joint member includes an overmolded dielectric element including an outer peripheral surface having an outer diameter and a pair of diametrically opposed knob members projecting radially from the outer peripheral surface; and wherein the female joint member includes an axial sleeve integral with and extending proximally from the second electrical contact, the axial sleeve including an inner peripheral surface having an inner diameter and a pair of diametrically opposed longitudinal slots terminating at a pair of oppositely extending circumferential slots sized for engageably but slidably receiving the knob members of the male joint member;

whereby the first and second electrical contacts are positively joined by axially aligning the connector pin and the connector ring while spaced apart, then advancing on axis the tail portion of the connector pin toward the connector ring so that the outer peripheral surface of the male joint member is fittingly engaged with the inner peripheral surface of the axial sleeve and so that the knob members are engaged with the longitudinal slots, then rotating the tail portion so that the knob members are engaged with the circumferential slots.

12. A connector assembly, as set forth in claim 7, including:

seal means intermediate the first and second electrical contacts for engaging a receiving orifice of the pulse generator.

13. A connector assembly, as set forth in claim 9, including:

first seal means intermediate the first and second electrical contacts for and overlying the tail portion of the connector pin and the engaging a receiving orifice of the pulse generator; and second seal means adjacent the first electrical contact and distant from the first seal means for engaging a receiving orifice of the pulse generator.

* * * * *